United States Patent
Bredno et al.

(10) Patent No.: US 8,340,744 B2
(45) Date of Patent: Dec. 25, 2012

(54) SYSTEM, APPARATUS, AND METHOD FOR REPRODUCIBLE AND COMPARABLE FLOW ACQUISITIONS

(75) Inventors: Joerg Bredno, San Francisco, CA (US); Alexandra Groth, Aachen (DE); Juergen Weese, Aachen (DE); Antonius Johannes Cornelius Bruijns, Best (NL); Peter Maria Johannes Rongen, Eindhoven (NL); Ronaldus Petrus Johannes Hermans, Den Bosch (NL); Heidrun Steinhauser, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1056 days.

(21) Appl. No.: 12/096,995

(22) PCT Filed: Dec. 8, 2006

(86) PCT No.: PCT/IB2006/054713
§ 371 (c)(1),
(2), (4) Date: Jun. 11, 2008

(87) PCT Pub. No.: WO2007/069166
PCT Pub. Date: Jun. 21, 2007

(65) Prior Publication Data
US 2008/0319309 A1 Dec. 25, 2008

Related U.S. Application Data

(60) Provisional application No. 60/750,728, filed on Dec. 15, 2005.

(51) Int. Cl.
*A61B 6/00* (2006.01)
*G06K 9/00* (2006.01)
*G06G 7/58* (2006.01)

(52) U.S. Cl. .......................... 600/431; 382/128; 703/11
(58) Field of Classification Search .................. None
See application file for complete search history.

(56) References Cited

U.S. PATENT DOCUMENTS 5,150,292 A * 9/1992 Hoffmann et al. ............ 600/431
(Continued)

FOREIGN PATENT DOCUMENTS

WO 93/15658 A1 8/1993
(Continued)

OTHER PUBLICATIONS

A.C. Santos, et al, "Estimation of Coronary Blood Flow by Contrast Propagation Using Simulated X-Ray Angiography", Computers in Cardiology, Sep. 1999, pp. 379-382.

(Continued)

*Primary Examiner* — Long V. Le
*Assistant Examiner* — Angela M Hoffa (57) ABSTRACT

A system, apparatus and method are provided for measuring and removing the influence of pulsatility on contrast agent flow in a region of interest of a vascular system of a patient. Once the change of blood speed over the cardiac cycle is known (pulsatility), this influence is removed from acquired image sequence for outcome control such that "quasi-stationary", regular flow acquisition is passed on to subsequent visualization and analysis processes. A contrast agent injector is also provided that simultaneously measures and uses ECG to inject a known contrast agent at a fixed point over the cardiac cycle or such that a known amount of contrast agent will arrive at a known time at a region of interest in the vasculature of a patient, thus controlling one of the main unwanted variables in an acquisition of blood flow sequences.

7 Claims, 8 Drawing Sheets

U.S. PATENT DOCUMENTS

| | | | |
|---|---|---|---|
| 5,413,105 A | | 5/1995 | Forestieri |
| 5,485,831 A | * | 1/1996 | Holdsworth et al. ......... 600/431 |
| 5,544,215 A | | 8/1996 | Shroy, Jr. et al. |
| 6,692,443 B2 | * | 2/2004 | Crutchfield et al. ......... 600/504 |
| 7,044,913 B2 | * | 5/2006 | Shiki ............................. 600/454 |
| 2001/0027265 A1 | | 10/2001 | Prince |
| 2005/0065432 A1 | | 3/2005 | Kimura |
| 2006/0004279 A1 | | 1/2006 | Ikeda et al. |
| 2008/0294038 A1 | * | 11/2008 | Weese et al. ................. 600/431 |

FOREIGN PATENT DOCUMENTS

| | | |
|---|---|---|
| WO | 01/22362 A1 | 3/2001 |

OTHER PUBLICATIONS

L.S. Rogers et al, "Automatic Fluid Velocity Detection Methods for Digital Angiography" Biomedical Engineering Conference, Apr. 1995, pp. 23-26.

* cited by examiner

SYSTEM, APPARATUS, AND METHOD FOR REPRODUCIBLE AND COMPARABLE FLOW ACQUISITIONS

The present invention relates to a system, apparatus, and method for acquiring information on blood flow that is both reproducible and comparable.

Blood is pumped through the body because pressure is imposed on the blood by the contraction of the heart. The instantaneous amount of pressure imposed on the blood depends on the contraction status of the heart, i.e., on the phase of the heart cycle. During systole the pressure is high, whereas the pressure might be nearly zero during diastole. Starting from the heart the time-varying pressure wave propagates through the vessel system leading to varying velocities $v(t)=v_{average}p(t)$ in the vessel system. The instantaneous blood propagation speed in the human vascular system strongly depends on the contraction status of the heart, i.e., on the phase of the heart cycle. The phenomenon is called the pulsatility p(t) of blood flow. The degree of pulsatility, here defined as the strength of variation of flow speed over the cardiac cycle, is an important functional parameter that gives the physician fundamental information about the actual state of the vascular system which includes but is not limited to:

Degree of arteriosclerosis/vessel wall compliance: A high degree of pulsatility shows that the vessel wall is not flexible any more and indicates calcification; and Risk factor for aneurysms: A high degree of pulsatility leads to strong varying pressure waves affecting the weakened vessel wall.

In addition, pulsatility p(t) influences and obscures functional parameters that describe other aspects of blood flow and perfusion. If the dependency of these other functional parameters on pulsatility is describable, one can compensate for the effects of pulsatility. As a result, the measurement of such functional parameters becomes more reliable and reproducible, e.g., allowing a better comparison of pre- and post-treatment parameters. An example is the instantaneous volumetric blood flow $Q(t)=Q_{average}p(t)$.

Despite its clinical relevance no methods have yet been established that estimate the degree of pulsatility from routinely acquired angiographic image sequences. That is, there is no generally accepted way for a physician/interventionalist to use acquired data for reliable and reproducible estimation of pulsatility and/or degree of pulsatility mainly from contrast agent density variations resulting from injection of a contrast medium. In providing such a technique or model, the model describing the influences of pulsatility for the mixing of blood and contrast agent and the transport of this mix in the vascular system under the influence of pulsatility must be adapted to the acquired observations that show the advance of contrast agent through a vascular system such that model parameters characterize the pulsatility. As one possibility, a time-intensity-curve of the concentration of contrast agent extracted at or near the point of contrast agent injection can be used as a feature that is input to this analysis.

Blood flow visualization and measurements are essential for assessing the severity of diseases in arteries (e.g. stenoses or aneurysms). One important application is blood flow assessment that is based on the visualization of the intra-arterial contrast bolus in contrasted diagnostic acquisitions of vasculature. Examples are given for the case of interventional x-ray but not intended to limit the applicability of the described methods and apparatus to this clinical application. In a minimally-invasive procedure an interventional radiologist inserts a catheter into the vessels of interest and injects contrast agent to make the blood flow visible in a sequence of images. Subsequently, the physician assesses the blood flow by a visual inspection of the spreading of the contrast agent in the recorded image sequence. Due to the pulsatile nature of blood flow the instantaneous propagation speed of the bolus strongly depends on the phase of the heart cycle. During the systole the contrast agent will be quickly pushed forward, whereas the bolus might even come to rest during the diastole. Diminishing the influence of the heartbeat eases the evaluation of the relevant physiologic information. As a result, blood flow assessment becomes easier and more reliable for the physician. Additionally, the dependency on injection point and time is reduced making the blood flow assessment more reproducible and allowing a better comparison of pre- and post treatment angiograms for outcome control.

Experiments on clinical data show that prior art image analysis methods to quantify contrast agent (CA) dynamics do not always give reproducible results. However, without such reproducibility, even a comparison pre- and post-intervention as outcome control is not valid. As major cause for non-reproducibility, a dependency of the CA dynamics to heart pulsatility was detected. Especially for elderly patients with increasing degree of arteriosclerosis, the vessel wall compliance is reduced and, consequently, blood flow in arteries shows strong variation over a heart cycle respective to the varying driving pressure in the aorta.

Given this condition and an arbitrary start of a contrast agent injection, a videodensitometric assessment of blood flow dynamics depends on the phase in the cardiac cycle when the CA bolus front has passed a diagnostically relevant region of interest in a vascular substructure. In the aorta, an oscillating flow velocity v(t) 1202 in vessels with reduced compliance is estimated.

A technique is needed that provides the physician/interventionalist with a technique that is able to measure pulsatility without any changes in the workflow and in the setup, uses this measurement of pulsatility to correctly subtract out of images the dependency of bolus propagation on the instantaneous phase of the heartbeat, and that provides a means for timing CA injection such that the effect of a patient's heart beat is reduced. Further, there is a need for a technique that can be used for a comparison of acquisitions before and after an interventional step and to separate the influences of the total blood flow amount and its pulsatility over the cardiac cycle.

The present invention provides a system, apparatus, and method for acquiring information on blood flow that is both reproducible and comparable. In the acquisition of such blood flow, for the physician/interventionalist the degree of pulsatility is an important functional parameter that among other clinical information:

indicates the actual state of the vascular system, e.g. the degree of arteriosclerosis or the vessel wall compliance;

provides one risk factor for aneurysms; and influences and obscures other functional parameters like the volumetric blood flow.

Hence, it is essential to determine functional parameters that take into account pulsatility and make these functional parameters more reliable and reproducible, e.g., allowing a better comparison of pre- and post-treatment parameters.

A first embodiment of the present invention provides the physician with a system, apparatus and method that is able to measure pulsatility from angiographies without any changes in a workflow and setup. The present invention provides a measurement of pulsatility from angiographies that is easily applicable to clinical sequences and may be performed fully automatically. In addition, estimation of pulsatility is a prerequisite for a reliable and reproducible blood flow assessment.

In the first preferred embodiment, the pulsatility and/or the degree of pulsatility is estimated primarily from contrast agent density variations resulting from injection of the contrast medium. A model describing mixing of blood and contrast agent and the transport of contrast agent in the vascular system under the influence of pulsatility is adapted to a time-intensity-curve. The model comprises all relevant parameters for the characterization of pulsatility and incorporates, in particular, the influences of pulsatility on the mixing of blood and contrast agent and for the transportation, by the flowing blood in a patient, of contrast agent having varying velocities.

In an alternative first embodiment, additional information is taken into account including the duration of each heart cycle extracted from a simultaneously recorded ECG signal.

The basic idea of a second embodiment is to replay the acquired x-ray sequence according to a time axis transformation making the visualization and subsequent processing of this bolus propagation less dependent on the instantaneous phase of the heartbeat. The influence of pulsatility is removed from the acquired image sequence for outcome control such that "quasi-stationary", regular flow acquisition is passed on to subsequent visualization and analysis processes. The characteristic parameters can be determined automatically (e.g. by image processing, preferably using the first embodiment described above or using ECG information) or selected by the end-user. For an optimal image quality of the replay and for a minimal dose exposure of the patient a time varying frame rate or a high frame rate with varying dose should be used for the acquisition of the angiograms. In doing so, the same time axis calibration as for the replay can be exploited.

In an extension of the proposed approach an improved outcome control is conducted by the comparison of adjusted pre and post treatment angiograms. To this end, both replay sequences have to be temporally adjusted to compensate for pulsatility such that the bolus starts from a given reference location (e.g. injection point) at the same time. Subsequently, the sequences are replayed to the physician in comparison or after respective subtraction if a visualization of the differences in blood flow after an intervention step is desired.

In the assessment of blood flow the physician has to take into account that the displayed propagation of the bolus is influenced by both physiological parameters indicating the degree of the disease (like blood flow obstructed by a stenosis, i.e. a local reduction of the cross section) and the phase of the heartbeat. The superimpositions of both as well as the different time scales due to the pulsatile nature of blood flow complicate assessment of flow sequences and diagnosis. Hence, the second embodiment provides an improved display of flow sequences to the physician by reducing the dependency of the bolus propagation from the instantaneous phase of the heart cycle. Since the bolus propagation is then also less dependent on the injection point and time, the procedure becomes more reproducible and allows a better outcome control by the comparison of pre- and post treatment angiograms.

Since there is a growing demand for functional information, the functionality of the second embodiment and its alternatives are important extensions of the application range of the first embodiment. The new time axis transformation can easily be added to planned perfusion and flow software packages and increases the value of angiograms for diagnoses and outcome control. One of the most important applications of the proposed method is visualizing differences in blood flow before and after an intervention. Note that this comparison is impossible if the proposed sequences are simply subtracted from one another, in which instance the sequence would be massively obscured by the fact that slow and fast flow time spans intermingle with different frequencies because of the effect of the patient's heart beat.

In a third embodiment, the control of the CA injection is based on an ECG analysis. When the physician/interventionalist initiates the contrast agent injection, the injector does not start immediately, but rather starts automatically at a next appearance of a pre-defined cardiac phase in a live-observed ECG.

This third embodiment can be used for achieving:
outcome control based on comparison of CA dynamics pre- and post intervention which is possible if a reproducible CA injection is provided.
different injector patterns can be adapted to the current heart rate and assessment algorithms can request the phase in the cardiac cycle when an observed bolus front arrives at a region of interest in a vascular subsystem.
the automated control of short contrast agent bursts, such that a flow dynamic at a pre-selected phase in the cardiac cycle can be assessed.

It is to be understood by persons of ordinary skill in the art that the following descriptions are provided for purposes of illustration and not for limitation. An artisan understands that there are many variations that lie within the spirit of the invention and the scope of the appended claims. Unnecessary detail of known functions and structure may be omitted from the current descriptions so as not to obscure the present invention. This is especially true of implementation details, even though some such implementation details are included in a drawing for an injection pump, this is a preferred mechanism. However, such a pump is not the only control mechanism and is used herein for expository purposes only.

In order to make blood flow visible in a sequence of images, the physician/interventionalist injects contrast agent into the vessels of interest which is subsequently imaged with an acquisition modality with sufficient temporal resolution. Such modalities include but are not limited to x-ray angiography, ultrasound, computed tomography and magnetic resonance imaging. In such acquisitions, the appearance of contrast agent in the image sequence is influenced by different pulsatility mechanisms:

A. Transformation of original injection pattern at injection point: At the injection point, contrast agent and blood is mixed. According to the ratio of these components, the vessel appears on the x-ray image with certain intensity $I_0(t)$. However, the ratio of components changes subject to the instantaneous volumetric blood flow $$Q_{feed}(t) = Q_{average} p(t). \quad (1)$$

Figure 1:
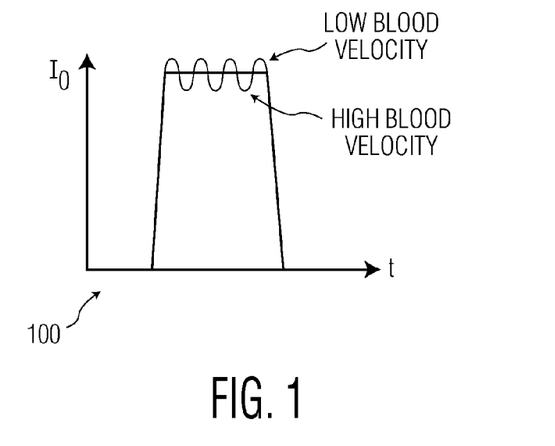
FIG. 1: Comparison of injection pattern (black) and time intensity curve at injection point (pulsatile initial injection, grey)

Hence, if this quantity is high, the fraction of blood is higher and therefore the attenuation of the vessel on the x-ray is lower. When the instantaneous volumetric blood flow is low the fraction of blood is also lower and the attenuation of the vessel is higher (FIG. 1).

B. Transporting contrast agent with varying velocities: Since the instantaneous velocity depends on the current phase of the heart cycle and the distance to the centerline of the vessel, contrast agent is transported with varying velocities. As a result, the appearance of contrast agent is not only modified on its way from the injection point to the observation point by effects like diffusion, but also due to pulsatility.

A method for a preferred first embodiment of the invention comprises the following steps:

1. Injecting contrast agent: via a catheter into the vessel tree of interest. The injection point may not be visible on the x-ray image and the distance L between injection and a suitably chosen observation point can be an additional model parameter (FIG. 2).
2. Recording of ECG: is not necessarily required. However, by extracting the duration of each heart cycle from the ECG signal the number of parameters of the pulsatility model is reduced.
3. Extracting time intensity curve $I_1(t)$ at the observation point which determines the concentration of contrast agent at this point over time: by averaging the intensity in a certain area around the observation point in a vessel in order to reduce the influence of noise.
4. Setting up of an appropriate model for the transport of contrast agent under the influence of pulsatility p(t): A suitable model has to comprise the different influences of pulsatility like the Pulsatile initial injection and
Pulsatile contrast agent transfer (CAT).

Figure 2:
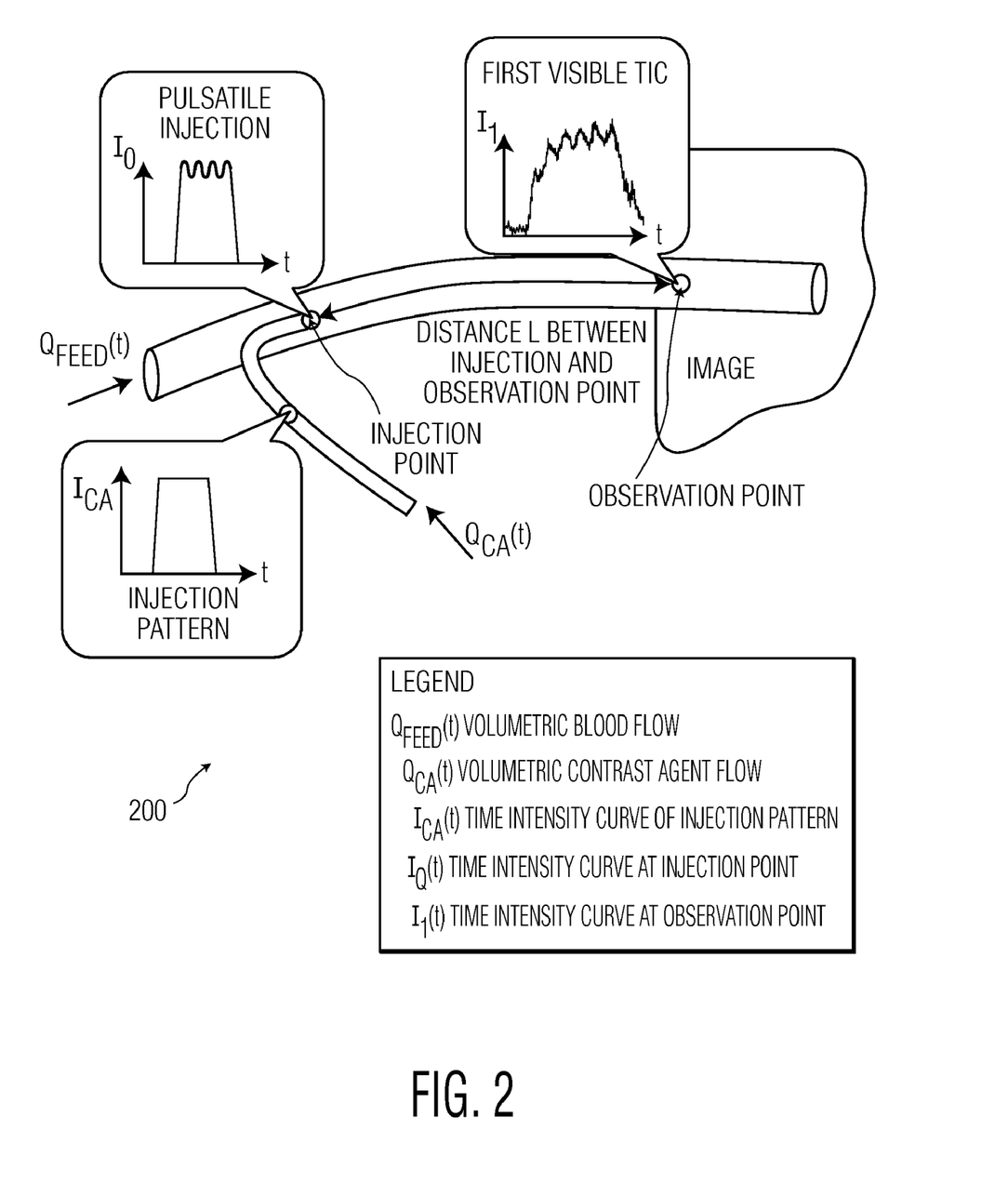
FIG. 2: Setup for the pulsatility measurement.
Figure 3:
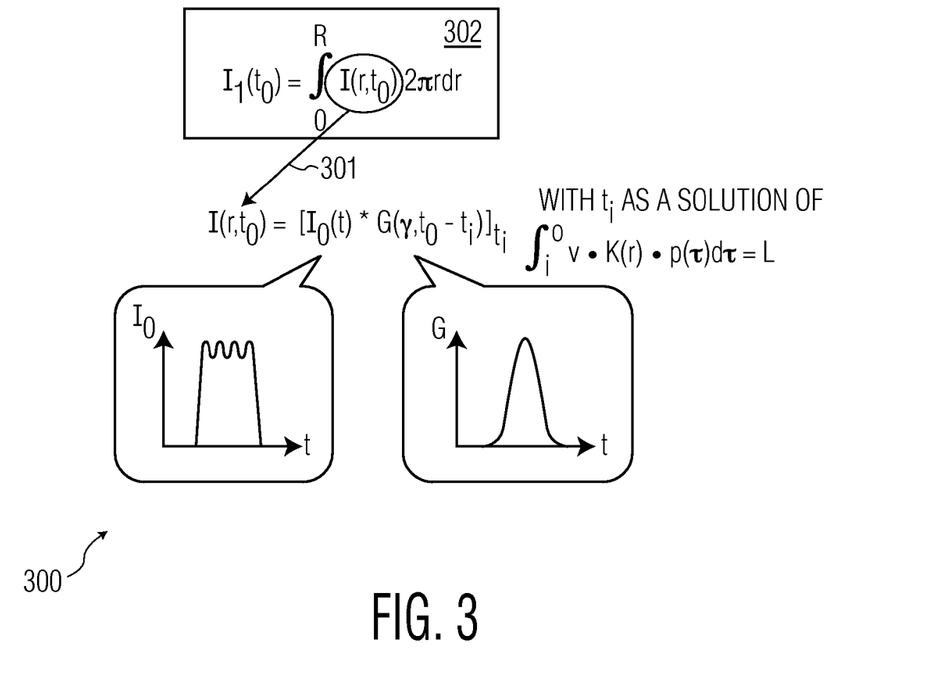
FIG. 3: Calculation of the time intensity curve $I_1(t)$ at an observation point downstream of the injection site.

Via the resulting model, a prediction of the time intensity curve at the observation point is possible. An exemplarily pulsatility model is described in the following:

a) The pulsatile injection $I_0(t)$, which is the time intensity curve at the injection point (FIG. 2), depends on the ratio of contrast agent (CA) and the overall amount of fluid (blood and CA). Due to pulsatility the amount of blood $Q_{feed}(t)$ $$I_0(t) = \frac{c_{CA} Q_{CA}(t)}{Q_{CA}(t) + \overline{Q}_{feed} p(t)} \quad (2)$$

according to Eq. 1 at the injection point is time dependent, whereas the amount $Q_{CA}(t)$ of CA is only time varying if the injection pattern is not a rectangular impulse. Templates for the pulsatility $p(\varnothing_{ECG})$ in dependency of the phase $\varnothing_{ECG}$ in the cardiac cycle are readily available for all observable vascular subsystems in the human body. For each observation, these templates have to be scaled and shifted in p and Ø-direction to reflect changes in the total blood flow, the degree of pulsatility, and a temporal offset from the ECG signal to the observed curve. From the observation itself or additionally acquired ECG, the phase in the cardiac cycle can be determined as $\varnothing_{ECG}(t)$ for each time of observation to construct the target p(t). Parameters like $c_{CA}$ further describe the influence of contrast agent on image values (if the system is not calibrated beforehand), $Q_{CA}$ (if the injection pump does not give the volumetric contrast agent flow) and $Q_{Average}$ are additional parameters in the optimization routine that are not directly related to pulsatility. When the contrast is injected through long, thin, flexible catheters, then the contrast agent at the injection site follows the contrast agent injector with a dampening and delay that is represented by a T1 control element. Here, the strength of this effect can be determined beforehand when the catheter is known.

b) After the pulsatile injection $I_0(t)$ the CA is subject to a pulsatile contrast agent transfer. The intensity $I_1(t_o)$ at the observation point at any observation time $t_o$ is obtained by integrating the intensity values $I(r,t_o)$ over the vessel lumen (FIG. 3, top). The intensity $I(r,t_o)$ is basically determined by the contrast material (with the associated intensity $I_0(t)$) that was injected at the injection time $t_i$ and that has covered the distance L between injection and observation point at the observation time $t_o$. Thus, the respective injection time $t_i$ is obtained by solving the equation $$\int_{t_i}^{t_o} v(\tau, r) d\tau = \int_{t_i}^{t_o} v_{average} \cdot \kappa(r) \cdot p(\tau) d\tau = L.$$

Here, $\kappa(r)$ represents the varying velocity of the blood and contrast agent over the vessel cross section. However, the transport of contrast agent is not only influenced by pulsatility but also by diffusion. The diffusion of contrast agent is simulated by a Gaussian distribution curve $G(\gamma, \Delta t)$ where $\gamma$ indicates the strength of the diffusion and $\Delta t$ is the duration of the diffusion (FIG. 3, element 301). Hence, additional model parameters are required to model the effects of pulsatile contrast agent transfer. These parameters are $\gamma$, L, $v_{Average}$ and $\kappa(r)$. Preferably, the degree of pulsatility $\Pi$ is defined such that $\Pi=0$ indicates stationary flow without pulsatile modifications and $\Pi=1$ indicates a complete stop of the flow in diastole. A degree of pulsatility above 1 would then indicate backflow and would be characterized by some values p(t) below 0.

Figure 4:
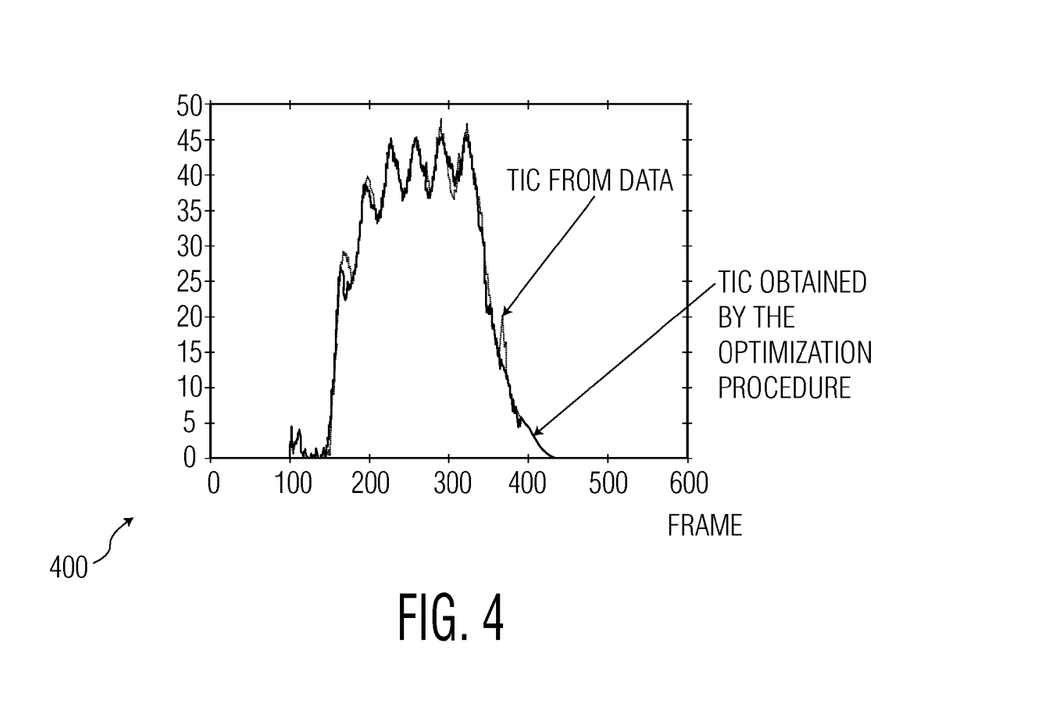
FIG. 4: Example for a measured time intensity curve and the corresponding model fit of the preferred analysis method.

5. Optimizing the model parameters: The pulsatility model makes a prediction of the time intensity curve at the observation point. In an optimization procedure the prediction and the observation are compared and the model parameters are adjusted such that the error between the measured time intensity curve and the model prediction is minimized, see FIG. 4.
6. Displaying results: to the physician/interventionalist in an appropriate way. Alternatively, results can be passed on to algorithms that require the compensation of pulsatility.

Alternative first embodiments reduce the number of mechanisms that influence the transport of contrast agent due to pulsatility. As a consequence, the associated model parameters become superfluous and the prediction by the pulsatility model becomes more precise: In particular, the injection point and observation point are identical. Thus, only the mixing of blood and contrast agent has to be represented by the model. If the system is calibrated beforehand by imaging a contrast agent probe, and, if the injection pump provides the volumetric contrast agent flow, no model adaptation is required at all. In this latter alternative embodiment, an observation $I_0(t)$ and all model parameters ($c_{CA}$ and $Q_{CA}(t)$) except the pulsatile volumetric blood flow $Q_{feed}(t)$ are known.

Hence, a direct calculation of $Q_{feed}(t)$ is possible (computed using equation (2) or step 4 of the above method).

The volume flow, degree of pulsatility, varying speed over a vessel cross section and diffusion parameters are adapted by a computer program to automatically determine these and provide them to a user.

Estimation of the pulsatility provides important information in itself. In addition, it supports reliable and reproducible blood flow assessment.

Figure 7:
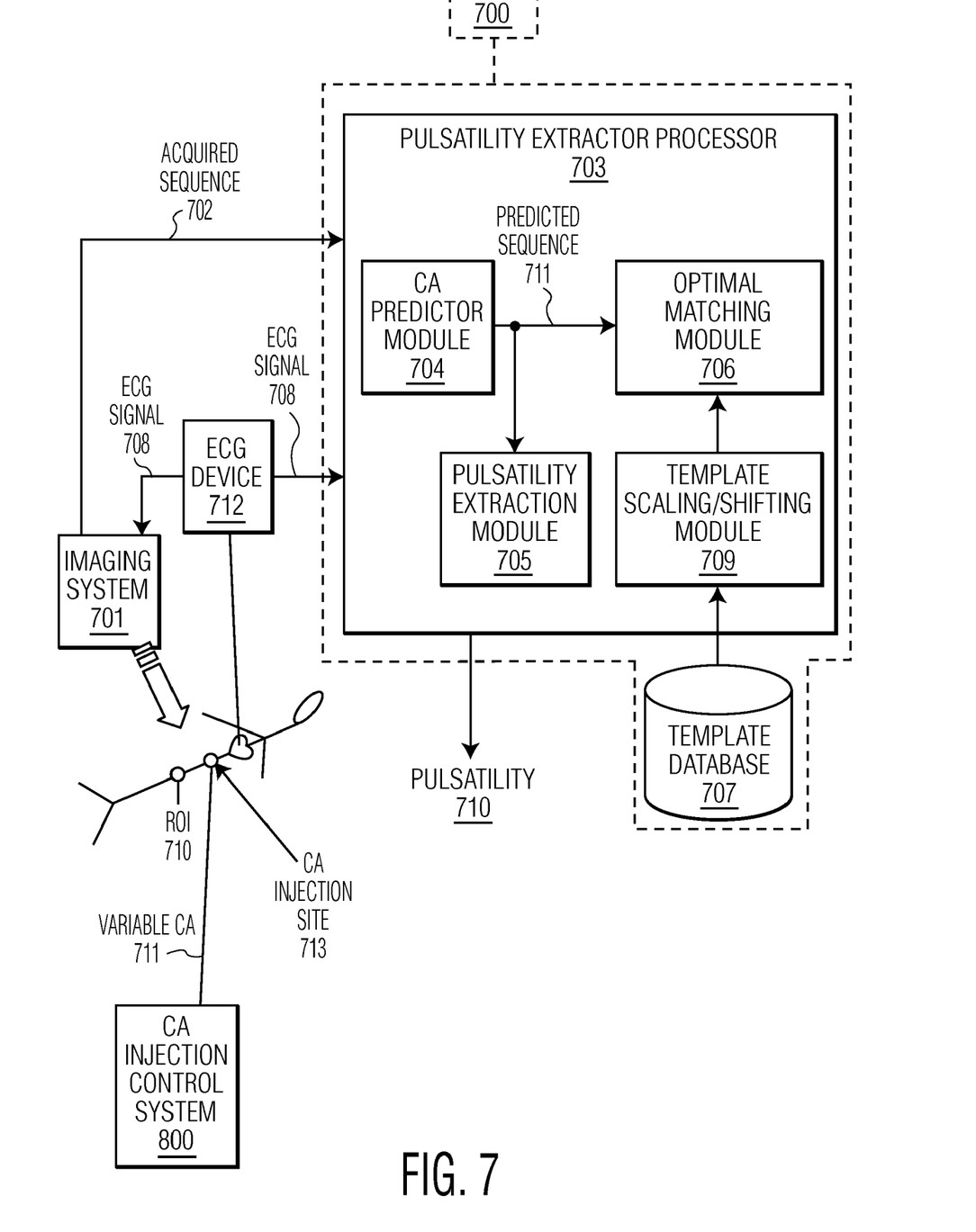
FIG. 7 illustrates an apparatus for extracting pulsatility from an acquired sequence of images according to the present invention.

Referring now to FIG. 7, an apparatus 703 is illustrated for extracting pulsatility from an acquired sequence of images 712, comprising a processor 703 configured to receive an ECG signal 708 and the image sequence 702, and to control the extraction of pulsatility therefrom by several modules. The modules include a contrast agent predictor module 704 for providing a predicted sequence, a template scaling/shifting module 709 that retrieves and transforms an appropriate template from a database of pre-defined templates 707 that covers all observable vascular subsystems in the human body and appropriately scales and shifts it, and a pulsatility extraction module 705 that compares the acquired sequence with the predicted sequence and derives a model in which the error therebetween is minimized. A model of a patient's pulsatility is output 710 that is based on the acquired sequence and ECG and is therefore only valid for the procedure performed.

The acquiring step may further comprise the step 711 of varying a concentration of the contrast agent over time at an injection site thereof, imaging 701 the known contrast agent at the injection site 713 to obtain an observed sequence of a concentration thereof, and obtaining a predicted sequence of the concentration of the known contrast agent at the injection site 713 by use of the contrast agent predictor module 704, and matching 706 the observed sequence with the predicted sequence.

A second preferred embodiment replays an acquired image sequence according to a heartbeat dependent time axis transformation. In doing so, the influence of the pulsatility on the displayed flow sequence is reduced. Its characteristic parameters are estimated by image processing methods from the sequences or selected by the end-user. The required information about the heart cycle is, for instance, extracted from the ECG Signal.

In an alternative second embodiment, pre- and post-treatment angiograms provide improved outcome control by the comparison of both adjusted replay sequences derived therefrom. To this end, both replay sequences are temporally adjusted such that the bolus starts from a given reference location (e.g. injection point) at the same time and the influence of pulsatility is removed using the time axis transformation. Subsequently, the sequences are replayed to the physician for comparison thereby.

In yet another alternative second embodiment, for an optimal image quality of the adjusted replay sequence at least one of a time varying frame rate or a high frame rate in combination with a varying tube current (allowing generation of the desired image frames after acquisition) is used for the acquisition of the angiograms. In doing so, the same or a similar time axis calibration as exploited in the replay of the blood flow sequence should be utilized for the variation of the frame rate or the tube current. The merits of this acquisition protocol are:

that the replayed frames are directly obtained in the x-ray procedure or that at least a sufficient number of frames/high dose angiograms are acquired during the essential phases of the heart cycle, respectively.

that the dose exposure of the patient is reduced by avoiding superfluous acquisitions or by minimizing the dose. In addition, the warming-up of the x-ray tube is eased.

Figure 5:
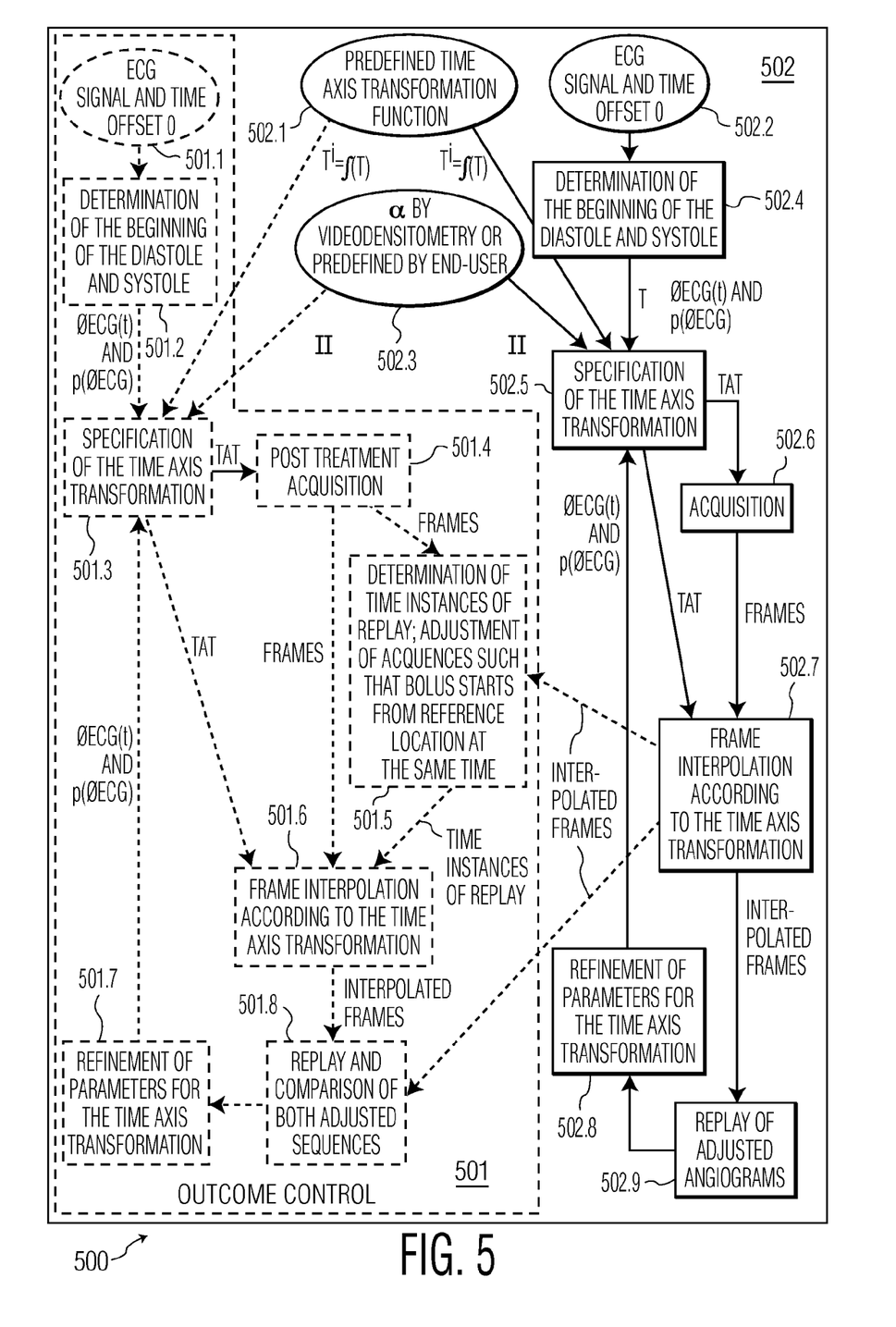
FIG. 5: Modified workflow for the enhanced displaying of x-ray flow sequences (TAT=time axis transformation)

A method according to the second embodiment is illustrated in FIG. 5, in which a replay of adjusted pre- and post-treatment angiograms is indicated by the dashed lines marking the related processing steps. The method comprises the steps of:

1. Specifying a time axis transformation 502.5: The blood flow is characterized by a change of the flow speed over the cardiac cycle that is represented in a curve $p(\emptyset_{ECG})$ which is transformed to a curve $p(t)$ via observations of the patient's cardiac activity, e.g. by ECG. This curve has to be appropriately scaled, an average speed has to be added and a phase shift or respective delay has to be applied such that a modified template curve $p(t)$ then represents the blood flow in a given observation. This modification is a linear transformation of the template curve such that in average, the volume flow Q is obtained that flows with a degree of pulsatility Π. Preferably, the degree of pulsatility Π is defined such that Π=0 indicates stationary flow without pulsatile modifications and Π=1 indicates a complete stop of the flow in diastole. A degree of pulsatility above 1 would then indicate backflow and would be characterized by some values $p(t)$ below 0.

2. Acquiring a sequence of images 502.6: In order to obtain a constant frame rate for the replay after the time axis transformation, a non-equidistant sampling of the time of the real world is required. To be more precise, the sampling of the real world axis is close, but equidistant during the systole and wider during diastole. Since the time transformation affects the time instances of acquisition, the time axis transformation might also steer the acquisition. To this end, two different possibilities exist:

a. The frame rate is adaptable. Hence, the images are acquired only at or close to the predefined time instance.

b. A high frame rate in which the desired image frames are generated after acquisition by binning/integrating. Additionally, the frame rate interpolation becomes easier since it ends up in a modified binning of the acquired frames.

3. Determining the beginning of the systole and diastole 502.4: The time axis transformation has to be conducted for each heart cycle separately. To this end, the phase on the cardiac cycle $\emptyset_{ECG}(t)$ has to be determined first. One possibility to obtain the required $\emptyset_{ECG}(t)$ consists in exploiting an ECG signal. Preferably, the phase is assigned by equal spacing between subsequent R-peaks in this ECG. When this method is applied, then the phase shift or delay of the ECG signal to the resulting flow speed in the observation is one parameter that can be manually adjusted or automatically determined such that the predicted time-intensity curves best match the extracted ones.

4. Interpolating the frame according to time axis transformation and replay 502.7: The time-axis transform t→t' is now defined according to $$\int_0^{t'} p(\tau) d\tau = t.$$

Due to the proposed time axis transformation the time instances of acquisition are not equidistant any more, since in general the frames have not been taken at exactly these required time instances (possibly not even in case of the modified acquisition protocols), a calculation of the intermediate frames is needed. To this end, a frame rate interpolation can be utilized. However, if a high frame rate in combination with a varying tube current is used, the frame rate interpolation ends up in a modified binning of the acquired frames. Subsequently after the frame rate interpolation, the images are displayed with respect to the new time scale t'.

5. Refining parameters 502.8: During inspection of the replay with respect to time scale t', the observer might notice imperfections due to a non-optimally estimated degree of pulsatility and phase shift of the template $p(\emptyset_{ECG})$. In consequence, the possibility to modify these parameters by user interaction can be provided by the replay system.

6. Controlling outcome 501: If, in addition a post treatment angiogram is available, the described approach above can also be utilized for an improved outcome control. To this end, the following steps are required:
   i. Determining time instances of replay 501.5: For a comparison of the bolus propagation in both sequences the bolus has to start from a reference location defined by the position of the catheter in the vasculature (e.g. the beginning of the aneurysm) at the same time. Since the injection point and time and the average blood flow velocity of both sequences is different, this demand does not apply in general to the acquired/adjusted sequences. Hence, the required time instances of replay for the post treatment sequence have to be determined first, before a time transformation can be conducted.
   ii. Transforming Time Axis 501.3 through Replaying and comparing adjusted time sequences 501.8—To achieve this, both sequences are preferably processed according to the processing described above for steps 1-5 but with individual time-axis transformations $t \rightarrow t_1'$ and $t \rightarrow t_2'$. As a final degree of freedom, in step 501.5, the temporal offset between the sequences is adjusted such that the observed time-intensity curves for one control point, preferably selected at the feed of a pathology, have maximum overlap.

As an example of the application of the second embodiment and its alternative, the goal of many vascular interventions is to beneficially modify the blood flow, e.g. to increase flow through a stenosed section or to reduce the blood stream in an aneurysm. A comparison of diagnostic and post-interventional acquisitions is therefore desired to judge the impact of an intervention. A visualization of differences can give valuable information of the type "contrast agent now arrives faster at this segment" or "the amount of attenuation in this segment is always reduced", which is available from a subtraction of pre- and post-interventional data.

To enable this subtraction, the influences of pulsatility and the moment of contrast injection have to be compensated for. For this compensation, a flow analysis of relevant sections of interest is required first, provided by using the first embodiment.

In the following example it is assumed that the average flow volumes Q1 and Q2 have been extracted together with their variation over time due to heartbeat and contrast injection in $p_1(t)$ and $p_2(t)$, respectively. Furthermore, TICs at the inflow into the relevant vascular substructure must be available. For comparable dynamic angiograms, an irregular re-sampling $t \rightarrow t_1'$ and $t \rightarrow t_2'$ is created such that:

$$\int_0^{t_i'} p_i(\tau) d\tau = t$$

This temporal re-sampling converts both acquisitions into quasi-stationary acquisitions that only vary in the total amount of blood flow. The temporal offset between the two sequences is determined that results in the maximal correlation of the TICs read at the inflow into relevant vascular substructure. The comparison of two diagnostic angiograms is further enhanced when the same amount of contrast agent is applied over the same injection time. Preferably, the injection starts in the same phase over the cardiac cycle. After this temporal registration and regularization, differences can be visualized with grayscale overlays and colored overlays on a post-interventional sequence.

Figure 6:
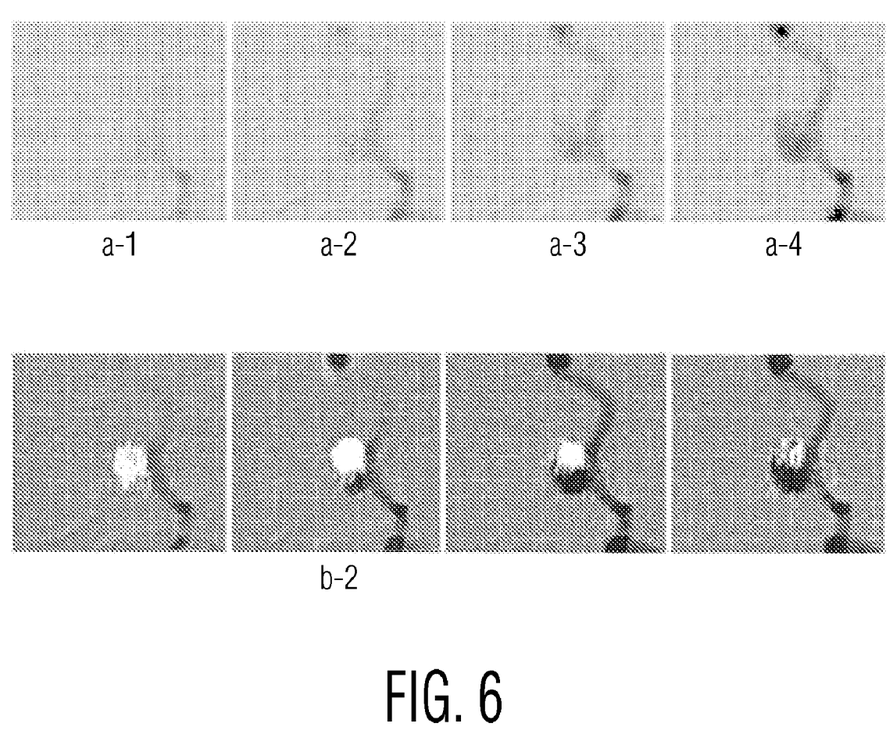
FIGS. 6a-b illustrate a comparison of pre- and post-intervention images using subtraction provided by the second embodiment.

Referring now to FIG. 6a-1 to 6a-4, an aneurysm in a neurovascular artery is simulated with an intervention of stent insertion such that the aneurysm flow fraction is reduced in the post-interventional simulation. Frames from the post-interventional acquisition are shown in FIG. 6a 1-4. After the temporal adjustment and registration described above, the subtraction images allow for comparison with a pre-interventional acquisition and reveal that contrast agent arrived earlier in the aneurysm before the intervention. This is coded as bright overlay in FIG. 6b-1 to 6b-4 and visualizes the effect of the intervention step, namely the slower flow of blood through the aneurysm.

A third embodiment provides a contrast agent injector for enabling reproducible and comparable flow acquisitions. The provided contrast agent injector measures ECG and always injects the contrast agent at a fixed point over the cardiac cycle, then at least the TICs at the injection site are similar, which removes one of the main unwanted variables in the acquisition of flow sequences.

In a third embodiment, the control of the CA injection is based on an ECG analysis. When the physician/interventionalist initiates the contrast agent injection, the injector does not start immediately, but rather starts automatically at a next appearance of a pre-defined cardiac phase in a live-observed ECG.

This third embodiment can be used for achieving:
   outcome control based on comparison of CA dynamics pre- and post intervention if a reproducible CA injection is provided.
   different injector patterns can be adapted to the current heart rate and assessment algorithms can request the phase in the cardiac cycle when an observed bolus front arrives at a region of interest in a vascular subsystem.
   short contrast agent bursts, such that a flow dynamic at a pre-selected phase in the cardiac cycle can be assessed.

Figure 8:
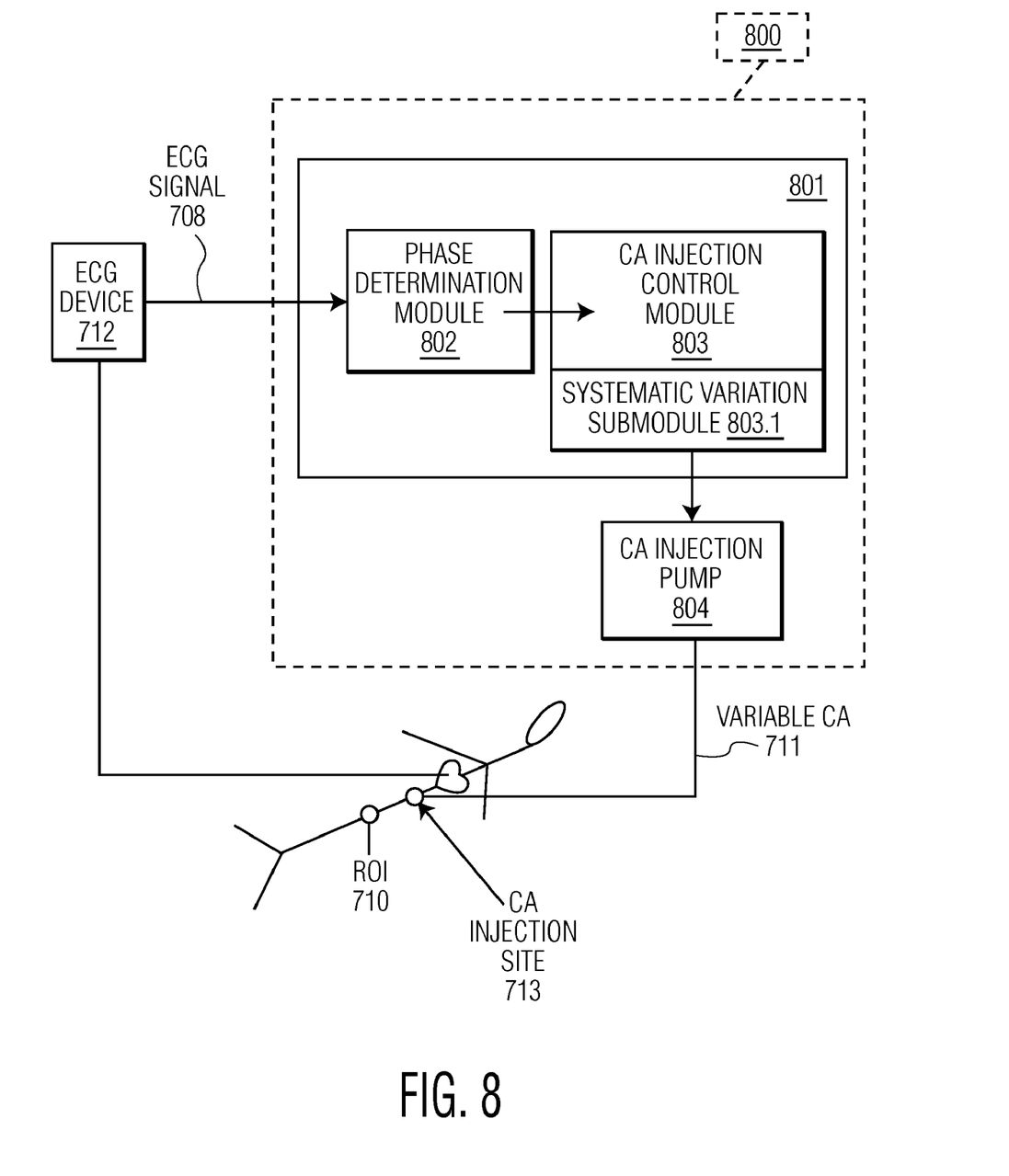
FIG. 8 illustrates an apparatus 800 according to a third embodiment.

An example of an apparatus 800 implementing the third embodiment is illustrated in FIG. 8, and provides a way to avoid the dependency of videodensitometric analyses on the time of injection. In a preferred third embodiment, control of the time of contrast agent injection is by a CA injection control module 802 and is based on ECG acquisitions 708. The QRS-complex or similar characteristics are detected on the acquired ECG signal 708 and, consequently, the heart rate and phase in the cardiac cycle is known, the latter through use of a phase determination module 803. With this information, the alternation of systolic and diastolic driving pressure in the vascular system is also known in advance. When activated by the physician/interventionalist, a CA control mechanism 804 (preferably an injection pump) does not start immediately, but the start is controlled by the control module 802 to occur at the next arrival of a pre-selected phase of the cardiac cycle, as determined by the phase determination module 803 from the simultaneously acquired ECG signal 708. This third embodiment requires a reproduced position of the injection point 713, which is preferably provided by at least one of imaging of the catheter itself and observation of the length to which the catheter is advanced.

An analysis system embodiment 900 comprises an integrated workstation 901 for quantitative or comparative analysis of CA dynamics and includes an integrated architecture of selected first through third embodiments and their alternatives of the present invention. For example, the workstation illustrated in FIG. 9 includes an ECG acquisition system 712, a CA injection control system 800 to provide start and stop commands for the CA injector and a dedicated image analysis subsystem 910 that adjusts to the current acquisition 712 and vice versa. This workstation 901 is further configured to update the estimation of the current phase in the cardiac cycle from live ECG acquisitions 712. Controls are included in a CA injection control system 800 that is interfaced to the workstation 901 so that the workstation can start and stop a contrast injection pump which synchronizes to the estimated current cardiac phase according to requirements pre-determined for specific analysis tasks.

Figure 9:
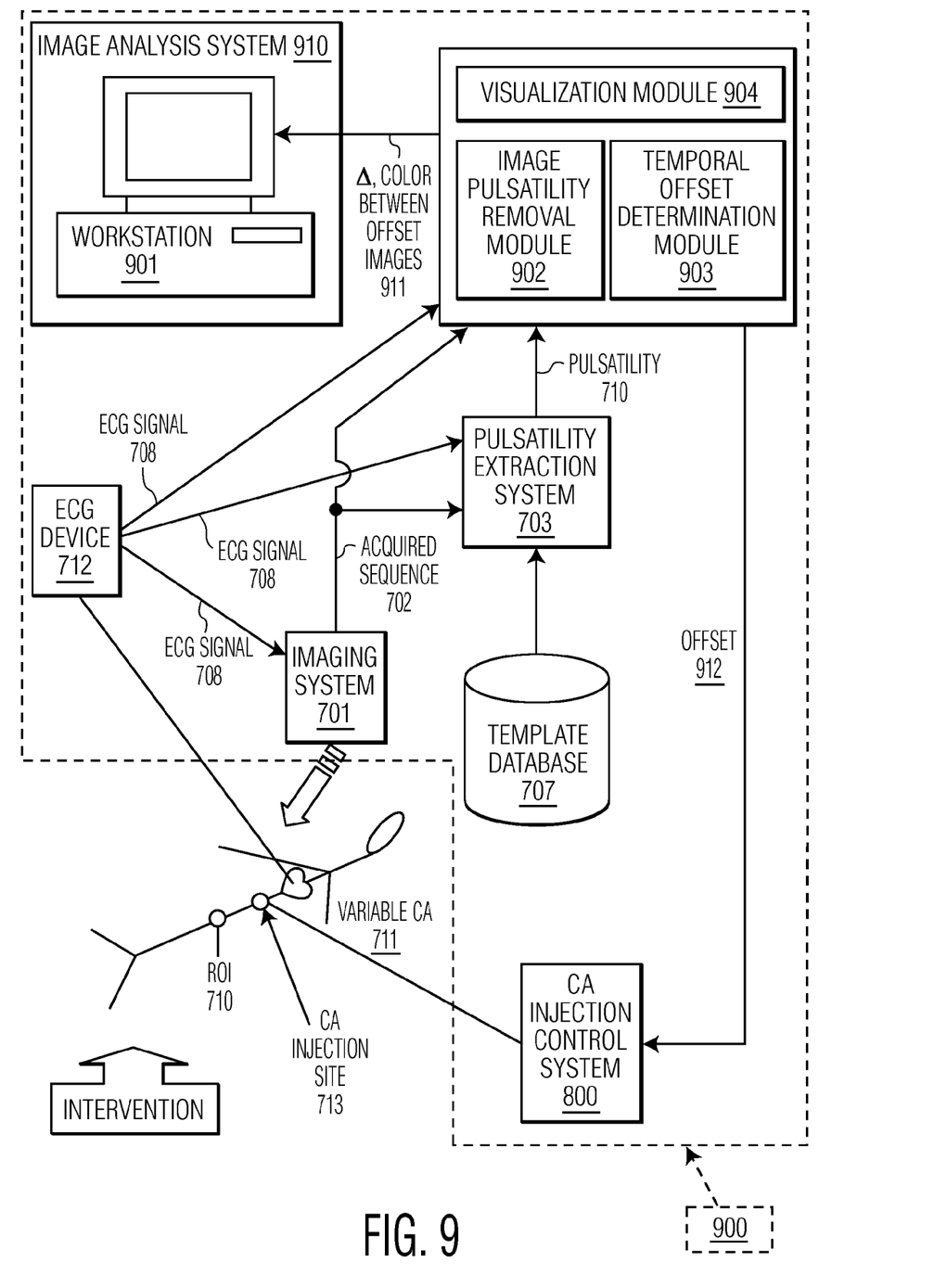
FIG. 9 illustrates an analysis system embodiment.

The system 900 includes a visualization module 904 for providing for visualization of data by the image analysis system 910, including providing a visualization of the difference 911 between the two sequences by the image analysis system 910. The visualization of the difference 911 may include the use of a color overlay. The visualization module 904 includes an image pulsatility removal module 902 removing image pulsatility, as described above. The visualization module 904 also includes a temporal offset determination module 903 determining an offset 912 as described above with reference to FIG. 7. The temporal offset determination module 903 communicates the offset 912 to the CA injection control system 800. The CA injection control administers CA at a variable rate 711 at the CA injection site 713 based on the offset 912 received from the temporal offset determination module 903.

Applications of the analysis embodiment include:

The introduction of patterns in the contrast agent injection $Q_{CA}(t)$ with an increased frequency in comparison to the heart beat can provide features of improved signal quality to analysis algorithms. The parameters of such an injection pattern can be controlled based on ECG and related information (e.g. heart rate) to allow for an improved adjustment of analysis algorithms and their respective injection patterns.

Short injector bursts at a defined phase can control the arrival of the CA bolus in a region of interest at pre-selected phases in the cardiac cycle. The systematic adjustment of the injection of such a small burst can give quantitative information regarding the blood flow dynamics at a region of interest over the full heart cycle. In a dedicated protocol, this short burst could be followed by a longer CA injection so that the vascular system and the CA dynamics are still visible to a human observer.

While the preferred embodiments of the present invention have been illustrated and described, it will be understood by those skilled in the art that the system, apparatus and methods as described herein are illustrative and various changes and modifications may be made and equivalents may be substituted for elements thereof without departing from the true scope of the present invention. In addition, many modifications may be made to adapt the teachings of the present invention to a particular situation without departing from its central scope. Therefore, it is intended that the present invention not be limited to the particular embodiments disclosed as the best mode contemplated for carrying out the present invention, but that the present invention include all embodiments falling within the scope of the claims appended hereto as well as all implementation techniques and not just the various implementation architectures used herein as examples.

The invention claimed is:

1. A method for visualization and analysis of an acquired time intensity sequence of images of a blood flow of the advance of a contrast agent through a region of interest in a vascular system of a patient, comprising the steps of:
   obtaining information on the pulsatile nature of the blood flow;
   modifying the acquired time intensity sequence of images using the obtained information to remove therefrom an influence of pulsatile flow, the modifying producing a modified sequence of images;
   determining a temporal offset between the acquired time intensity sequence of images and the modified sequence of images such that a concentration of contrast agent at a pre-selected point in time has maximal similarity between the two sequences of images;
   offsetting the modified sequence of images by the determined temporal offset; and
   providing both the acquired time intensity sequence of images and the offset sequence of images to an image analysis system.

2. The method of claim 1, wherein where the information on the pulsatile nature of the blood flow is obtained by performing a method comprising:
   acquiring, with an imaging system, the time intensity sequence of images, wherein the imaging system is selected from the group consisting of interventional x-ray, ultrasound, and repeated acquisitions using angiography with computed tomography or magnetic resonance imaging, the acquiring comprising the substeps of:
      varying a concentration of the contrast agent over time at an injection site thereof;
      imaging the contrast agent downstream of the injection site at the region of interest to obtain an observed sequence thereof; and
      simultaneously obtaining an electrocardiogram (ECG) signal from the patient;
   identifying a phase of a cardiac cycle of the patient from the ECG;
   obtaining a predicted sequence of the concentration of the contrast agent at the injection site from a contrast agent prediction model, wherein the contrast agent prediction model is based on a predetermined template as a function of the identified phase and the function further based on model parameters representing the transport of the mix of contrast agent and blood downstream of the injection site by each of convection, dispersion due to varying speeds over a vessel cross section, diffusion, and variable transport speed due to pulsatility;
   matching the observed sequence with the predicted sequence by adjusting the model parameters such that the error between the observed sequence and the predicted sequence is minimized; and
   extracting a degree of pulsatility from the adjusted model parameters.

3. The method of claim 2, wherein the template is a simplified template comprising a high average flow speed in systole and a low average flow speed in diastole.

4. The method of claim 3, wherein the acquired sequence of images comprises two sequences of images, the two sequences of images comprising a sequence of images acquired before an interventional step and a sequence of images acquired after an interventional step.

5. The method of claim 4, further comprising visualizing differences between the sequence of images acquired before the interventional step and the sequence of images acquired after the interventional step.

6. The method of claim 5, wherein the step of visualizing differences further comprises the step of using a color overlay for one of the two sequences of images.

7. The method of claim 6, further comprising the step of determining a temporal offset between the sequence of images acquired before the interventional step and the sequence of images acquired after the interventional step such that a concentration of contrast agent at a pre-selected point in time has maximal similarity between the sequence of images acquired before the interventional step and the sequence of images acquired after the interventional step.

* * * * *